US008652441B2

(12) United States Patent
Fukui et al.

(10) Patent No.: US 8,652,441 B2
(45) Date of Patent: Feb. 18, 2014

(54) CONTRAST AGENT FOR PHOTOACOUSTIC IMAGING AND PHOTOACOUSTIC IMAGING METHOD

(75) Inventors: Tatsuki Fukui, Yokohama (JP); Fumio Yamauchi, Yokohama (JP); Satoshi Yuasa, Yokohama (JP); Sachiko Inoue, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 457 days.

(21) Appl. No.: 12/893,074

(22) Filed: Sep. 29, 2010

(65) Prior Publication Data

US 2011/0081294 A1 Apr. 7, 2011

(30) Foreign Application Priority Data

Oct. 5, 2009 (JP) ................................ 2009-231999
May 31, 2010 (JP) ................................ 2010-124075

(51) Int. Cl.
*A61B 10/00* (2006.01)
*A61B 8/00* (2006.01)
*A61B 5/00* (2006.01)

(52) U.S. Cl.
USPC ............................ 424/9.6; 424/1.11; 424/9.1

(58) Field of Classification Search
USPC ............ 424/1.11, 1.61, 1.65, 9.1, 9.6; 540/1; 548/400; 568/18
See application file for complete search history.

(56) References Cited

U.S. PATENT DOCUMENTS 5,871,872 A * 2/1999 Matijevic et al. ................. 430/7
7,435,524 B2 * 10/2008 Anderson et al. ............. 430/138
8,337,809 B2 * 12/2012 Yu et al. ....................... 424/1.29
2010/0225314 A1 9/2010 Kuge et al. .................... 324/307

FOREIGN PATENT DOCUMENTS

JP H06-296612 10/1994

OTHER PUBLICATIONS

MP Mienkina et al., “Evaluation of Ferucarbotran (Resovist®) as a Photoacoustic Contrast Agent”, *Biomed. Tech.*, vol. 54, pp. 83-88 (2009).
G Kim et al., “Indocyanin-Green-Embedded PEBBLES as a Contrast Agent for Photoacoustic Imaging”, *Jour. of Biomed. Optics*, vol. 12, No. 4, 44020-1 through 44020-8 (Jul./Aug. 2007).
A Moore et al., “In Vivo Targeting of Underglycosolated MUC-1 Tumor Antigen Using a Multimodal Imaging Probe”, *Cancer Research*, vol. 64, pp. 1821-1827 (Mar. 1, 2004).

* cited by examiner

*Primary Examiner* — D L Jones
(74) *Attorney, Agent, or Firm* — Fitzpatrick, Cella, Harper & Scinto

(57) ABSTRACT

A method of detecting a contrast agent for photoacoustic imaging provides a high signal intensity. In a contrast agent for photoacoustic imaging, each particle containing an inorganic material supports at least an organic dye having an absorption coefficient in the near infrared region by means of chemical bonding.

17 Claims, 3 Drawing Sheets

CONTRAST AGENT FOR PHOTOACOUSTIC IMAGING AND PHOTOACOUSTIC IMAGING METHOD

BACKGROUND OF THE INVENTION

1. Field of the Invention

The present invention relates to a photoacoustic imaging method.

2. Description of the Related Art

Various imaging methods for imaging information on the inside of a living body (subject body) are known. Of these, the photoacoustic tomography described in Japanese Patent Application Laid-Open No. H06-296612 has been attracting attention because the photoacoustic tomography is a method capable of non-invasively acquiring a tomographic image without any risk of exposure to radiation. With the photoacoustic tomography, a probe beam is irradiated from a local surface spot of a subject body to be observed, the magnitude of the acoustic wave generated by the irradiated beam in the inside of the subject body (photoacoustic signal intensity) is measured and the results of the measurement are processed for imaging.

Mienkina M P, Friedrich C-S, Hensel K, Gerhardt N C, Hofmann M, Schmitz G: Evaluation of Ferucarbotran (Resovist®) as a photoacoustic Contrast Agent, Biomed Tech 2009; 54:83-88 reports the results obtained by observing the photoacoustic signals of a contrast agent containing iron oxide particles for MRI (magnetic resonance imaging) apparatus.

On the other hand, G. Kim, S. W. Huang, M. O'Donnell, R. Agayan, K. Day, M. Day, R. Kopelman and S. Ashkenazi, "Indocyanine Green embedded PEBBLEs as a Contrast Agent for photoacoustic Imaging", Journal of Biomedical Optics 12 (4) 044020 July/August (2007) reports the results obtained by preparing silica nano particles containing a dye by means of a sol-gel technique and observing the photoacoustic signals from them.

SUMMARY OF THE INVENTION

While Mienkina et al. observes the photoacoustic signals of a contrast agent containing iron oxide particles for MRI apparatus (tradename: Resovist, available from Nihon Schering), they are accompanied by a problem of low signal intensity.

Kim et al. observes the signal intensity of silica nano particles containing a dye. However, the dye is not chemically bonded to silica nano particles by covalent bonding or in some other form of bonding, and hence the observation gives rise to a problem that the signal intensity falls during the observation because of decomposition due to light irradiation.

In view of the above mentioned problems, in an aspect of the present invention, there is provided a contrast agent for photoacoustic imaging wherein each particle containing an inorganic material of the agent supports at least an organic dye having an absorption coefficient in the near infrared region by means of chemical bonding.

In another aspect of the present invention, there is provided a photoacoustic imaging method including: irradiating light in the wavelength region between 600 nm and 1,300 nm onto a subject body administered with a contrast agent for photoacoustic imaging, wherein an organic dye showing a molar absorption coefficient not less than 10 $M^{-1}cm^{-1}$ in the wavelength region between 600 nm and 1,300 nm is chemically bonded to particles having an inorganic material showing a molar absorption coefficient not less than $10^2$ $M^{-1}cm^{-1}$ in the wavelength region between 600 nm and 1,300 nm, and detecting the acoustic wave generated from the contrast agent existing in the subject body.

Thus, the present invention provides a contrast agent for photoacoustic imaging that shows excellent photoacoustic characteristics. This is because an organic dye is supported by particles having an inorganic material therein, and hence the signal intensity of the photoacoustic signals being observed is high and less falling compared to the prior art. The present invention also provides a photoacoustic imaging method using such a contrast agent.

Further features of the present invention will become apparent from the following description of exemplary embodiments with reference to the attached drawings.

DESCRIPTION OF THE EMBODIMENTS

Figure 1:
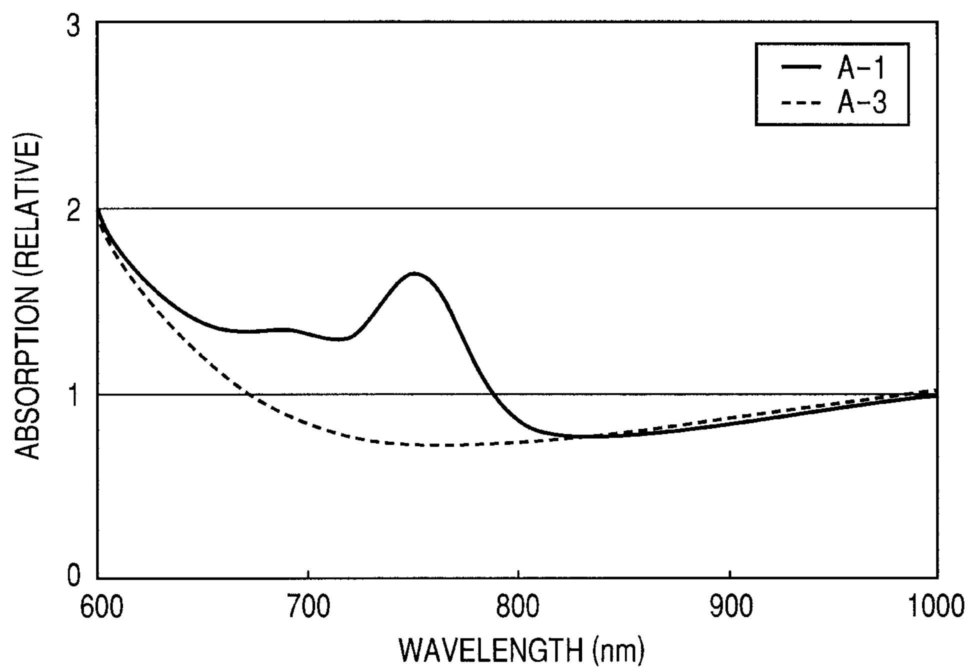
FIG. 1 is an illustration of the results of measurement of the light absorbance of the contrast agent for photoacoustic imaging of Example A-1 and that of the contrast agent of Comparative Example A-3.

Now, embodiments of the present invention will be described, although the present invention is by no means limited by the embodiment.

The contrast agents for photoacoustic imaging of the embodiments of the present invention are characterized in that at least an organic dye having an absorption coefficient in the near infrared region is, by chemical bonding, supported by a particle containing an inorganic material. The near infrared region refers to the wavelength region between 600 nm and 1,300 nm. The expression of having an absorption coefficient in the near infrared region refers to absorbing irradiated light in the wavelength region between 600 nm and 1,300 nm.

Embodiment 1

A contrast agent for photoacoustic imaging will be described for Embodiment 1.

The contrast agent for photoacoustic imaging of this embodiment is characterized in that an organic dye is chemically bonded to each particle having an inorganic material. Note that the particle having an inorganic material shows a molar absorption coefficient not less than $10^2$ $M^{-1}cm^{-1}$ in the wavelength region between 600 nm and 1,300 nm and is a material for generating a photoacoustic wave. The particle having an inorganic material can show a molar absorption coefficient not less than $10^{13}$ $M^{-1}cm^{-1}$. The organic dye is a material showing a molar absorption coefficient not less than 10 $M^{-1}cm^{-1}$ in the wavelength region between 600 nm and 1,300 nm and is a material for generating a photoacoustic wave. The organic dye can show a molar absorption coefficient not less than $10^8$ $M^{-1}cm^{-1}$.

That the particle having an inorganic material and the organic dye respectively show molar absorption coefficients not less than $10^2$ $M^{-1}cm^{-1}$ and not less than 10 $M^{-1}cm^{-1}$ in the wavelength region between 600 nm and 1,300 nm provides the following advantages. When the contrast agent of this embodiment is employed for a photoacoustic imaging method, the contrast agent is required to be highly absorptive to light in the wavelength region between 600 nm and 1,300 nm where the influence of absorption by and dispersion in living bodies is limited. Being highly absorptive specifically refers to that the molar absorption coefficient of the particle having an inorganic material is required to be not less than $10^2$ $M^{-1}cm^{-1}$ and the molar absorption coefficient of the organic dye is required to be not less than 10 $M^{-1}cm^{-1}$. When the molar absorption coefficients are large, they can absorb energy of irradiated light to a large extent so that it will be easy to assume that they can generate a large acoustic wave. Then, as a result, it will be easy to specifically locate the position of the contrast agent in the living body to which the agent is administered in the image obtained by means of a photoacoustic imaging method.

An organic dye is less liable to be decomposed by irradiation with light when the organic dye is chemically bonded to particles than when it stands alone. For this reason, the organic dye of this embodiment is hardly separable from the particles of the inorganic material because the organic dye is chemically bonded to the particles. Thus, the organic dye is substantially free from a risk of being decomposed. Additionally, a large number of organic dyes are preferably chemically bonded to the particles. More specifically, the number of organic dyes that are chemically bonded to the particles is preferably not less than 6, more preferably not less than 10. There are two reasons for that a large number of organic dyes are preferably chemically bonded to the particles. One is that energy of irradiated light is apt to be absorbed to a large extent when a large number of organic dyes are chemically bonded to the particles. The other is that light is likely to become quenched when a large number of organic dyes are put together so that the ratio of the energy emitted as fluorescence in the energy of irradiated light falls while the ratio of the energy that is transformed into thermal energy rises. Then, it will be easy to assume that more acoustic waves are generated when the number of organic dyes is large than when the number of organic dyes is small as a result.

For a photoacoustic imaging method according to the present invention, the wavelength of light to be irradiated can be selected by selecting a laser source to be used. Unlike an arrangement where an inorganic material is employed alone for a contrast agent for photoacoustic imaging, an absorption property that matches the wavelength of light to be irradiated can selectively be defined for the contrast agent by making organic dyes, of which many kinds are generally absorptive in the wavelength region of “the biological window”, to be supported by each particle of an inorganic material.

However, a contrast agent for photoacoustic imaging using such organic dyes is accompanied by a problem that the organic dyes can be decomposed to reduce the signal intensity during a measurement session when light is irradiated thereto. However, such decomposition of the organic dyes is suppressed to enable to stably measure a large acoustic wave by making them to be supported by particles having an inorganic material by way of chemical bonding.

For this reason, a contrast agent for photoacoustic imaging according to the present invention raises the degree of absorption in the wavelength region of “the biological window” by making the organic dye to be supported by particles of an inorganic material to enable to stably measure a large acoustic wave compared to when the inorganic material is employed alone.

(Particles Having an Inorganic Material)

Particles having an inorganic material in this embodiment refer to those solely made of the inorganic material, those in which the inorganic material is dispersed in an inorganic or organic compound or those in which the inorganic material is coated with an inorganic or organic compound. For the purpose of the present invention, particles of one of the above-described three types may selectively be used. Alternatively, particles of all or two of the above-described three types may be used in combination.

The inorganic materials include metal oxides, noble metal colloids, semiconductor particles, inorganic dyes and inorganic pigments. In this embodiment, it is sufficient for particles having an inorganic material to contain at least one of such inorganic materials. Alternatively, they may contain two or more of such inorganic materials. It is sufficient for particles having an inorganic material to contain at least an inorganic material. Alternatively, they may contain two or more than two inorganic materials.

Examples of the metal oxides include iron oxides ($Fe_2O_3$, $Fe_3O_4$), magnesium oxide, aluminum oxide, silicon dioxide, zinc oxide, titanium oxide, zirconium oxide, manganese oxide and boron oxide. The noble metals colloids used for this embodiment include colloidal gold, colloidal silver, colloidal copper and colloidal platinum. A mixture of two or more than two colloidal noble metals selected from colloidal gold, colloidal silver, colloidal copper and colloidal platinum may also be employed. The semiconductor particles include particles of cadmium sulfide, those of zinc selenide, those of cadmium selenide, those of zinc telluride, those of cadmium telluride, those of zinc sulfide and those of lead sulfide. The inorganic dyes include carbon black, fullerene and carbon nanotube. The inorganic pigments include iron oxalate. The inorganic material is preferably particles of iron oxide (iron oxide particles).

While the size of particles having an inorganic material may arbitrarily be selected, particles preferably show a mean particle size within the range between 1 nm and 1,000 nm. A blood clot can occur in the blood vessels of the subject body when the size exceeds 1,000 nm. A size between 10 nm and 200 nm is particularly preferable. The shape of particles of the inorganic material is not particularly limited and specific structures such as nano-rod, nano-cube, nano-prism and nano-shell may be utilized. An inorganic material may be used alone or, alternatively, two or more than two inorganic materials may be used in combination.

Organic compounds for dispersing or coating the inorganic material that can be used for this embodiment include polysaccharides, proteins, peptides, nucleic acids, synthetic polymers, liposome, polymer micelles, polyion complexes, fatty acids and surfactants.

Examples of polysaccharides include dextran, pullulan, mannan, amylopectin, chitosan, xyloglucan, hyaluronic acid, alginic acid, water-soluble cellulose, starch, agarose, carrageenan and heparin. Derivatives of polysaccharides obtained by introducing one or more of functional groups selected from amino group, hydroxyl group, carboxyl group, maleimide group and so on may also be utilizable.

Proteins include gelatin, collagen, albumin and fibrin.

The examples of synthetic polymers include polymers having amino groups such as polyethyleneimine, polylysine, polyarginine, polyhistidine, polyaryl amine and polyamide amine dendorimer, polymers having hydroxyl groups such as polyvinylalcohol and polyethyleneglycol, polymers having carboxyl groups such as polyglutamic acid, polyaspartic acid, polymalic acid, polymethacrylic acid, polyacrylic acid, polyfumaric acid and polymaleic acid, polymers having acid anhydride such as poly(maleic acid anhydride) and polymers having biocompatibility such as polylactic acid and polyglycolic acid.

Examples of phospholipids that constitute the liposome include phosphatidylcholine, phosphatidylserine, phosphatidylinositol, phosphatidylglycerol, posphatidylethanolamine and sphingomyeline.

Examples of polymers for forming polymer micelles include block copolymers having a hydrophilic segment of polyethylene glycol and a hydrophobic segment selected from a group of polylactide, poly(lactide-co-glycolide) and poly-$\epsilon$-caprolactone.

Examples of combinations of polymers for forming poly ion complexes include those of polymers having a polycation segment selected from a group of polyethyleneimine, polylysine, polyarginine, polyhistidine and polyaryl amine and polymers having a polyanion segment selected from a group of polyglutamic acid, polyaspartic acid, polymalic acid, polymethacrylic acid and polyacrylic acid.

Copolymers containing at least one of the above listed polymer units and having another unit originating in a monomer are also utilizable.

Examples of fatty acids include saturated fatty acids such as lauric acid, myristic acid, palmitic acid, stearic acid, unsaturated fatty acids such as lauroleic acid, physeteric acid, myristoleic acid, palmitoleic acid, petroselic acid and oleic acid and branched fatty acids such as isolauric acid, isomyristic acid, isopalmitic acid and isostearic acid.

Examples of surfactants include polyoxyethylene alkyl ether, alkyl sulfates, phospholipids and polyoxyethylene sorbitan-based fatty acid esters.

Examples of inorganic compounds for dispersing or coating the inorganic material include silica, carbonates and hydroxyapatites.

The organic compound or the inorganic compound for dispersing or coating the inorganic material may be used alone or mixed at an arbitrarily selected ratio.

Any desired size may be selected for particles having an inorganic material that can be used for this embodiment and there are no particular limitations to the size. Particles having an inorganic material that are solely made of the inorganic material and can be used for this embodiment have a size similar to that of the inorganic material. The size of the particles having the inorganic material dispersed in or coated with the inorganic or organic compound is preferably between about 1 nm and about 1,000 nm. A blood clot can occur in the blood vessels of the subject body when the size exceeds 1,000 nm. A size between 10 nm and 200 nm is particularly preferable.

(Organic Dye)

When the photoacoustic imaging method according to the present invention is applied to a living body, light of a wavelength in the range between 600 nm and 1,300 nm, which is referred to as "the biological window" where the influence of absorption by and dispersion in living bodies is limited, is irradiated in order to efficiently observe a photoacoustic wave. Therefore, the organic dye preferably is absorptive in the range of wavelength between 600 nm and 1,300 nm.

Examples of the organic dyes include azine-based dyes, acridine-based dyes, triphenylmethane-based dyes, xanthene-based dyes, porphyrin-based dyes, cyanine-based dyes, phthalocyanine-based dyes, styryl-based dyes, pyrylium-based dyes, azo-based dyes, quinone-based dyes, tetracycline-based dyes, flavone-based dyes, polyene-based dyes, BODIPY (tradename)-based dyes and HiLyte Fluor (tradename)-based dyes.

Examples of porphyrin-based dyes include Photofrin (available from Wyeth), Laserphyrin (available from MEIJI SEIKA) and Visudyne (available from Norvatis Pharmaceuticals), all of which are prescription drugs.

Examples of cyanine-based dyes include indocyanine green, Alexa Fluor (tradename)-based dyes (available from Invitrogen), Cy (tradename)-based dyes (available from GE Helthcare Bioscience), DyLight (tradename)-based dyes (available from PIERCE Biotechnology) and ADS832WS (available from American Dye Source).

Examples of phthalocyanine-based dyes include IRDye (tradename, available from LI-COR) and 2,11,20,29-Tetra-tert-butyl-2,3-naphthalocyanine (available from Sigma-Aldrich Japan).

Examples of HiLyte Fluor (tradename)-based dyes include HiLyte Fluor (tradename) 750 Bis-NHS ester and isomer II TEA salt.

The organic dye of this embodiment is preferably a compound expressed by one of the structures shown below.

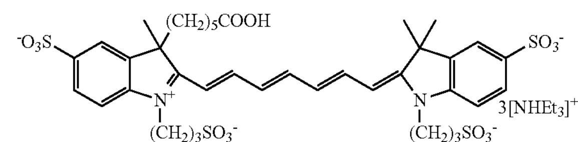

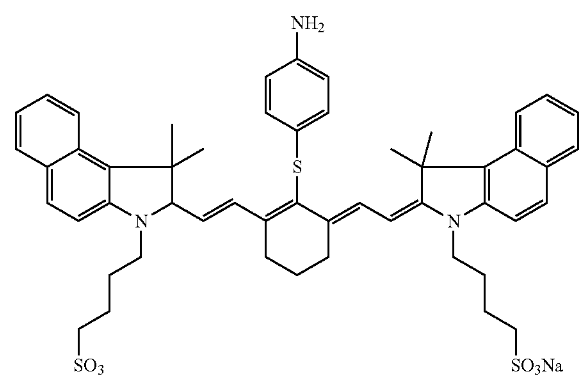

-continued

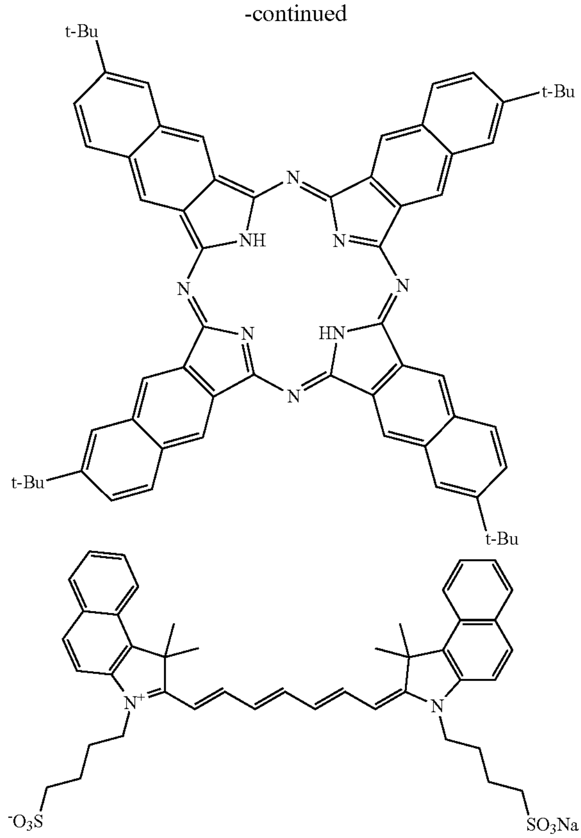

The organic dye of this embodiment may be used alone or appropriately mixed with some other dye.

(Support of Organic Dye)

Chemical bonding can be utilized to make particles having an inorganic material support the organic dye. The chemical bonding may be in the form of covalent bond, ionic bond, hydrogen bond, coordinate bond, hydrophobic interaction or stacking interaction.

That the organic dye is supported by chemical bonding means that the organic dye is bonded to the inorganic material by chemical bonding or that the organic dye is bonded to the organic compound dispersing or coating the inorganic material.

For example, the covalent bond may be an amide bond originating from a reaction between an amino group and a carboxyl group, an ester bond originating from a reaction between a hydroxyl group and a carboxyl group, a thioester bond originating from a reaction between a maleimide group and a thiol group or a sulfate ester bond originating from a hydroxyl group and a sulfonic acid group.

The ion bond may be a bond originating from an acidic group such as a carboxyl group or a sulfonic acid group and a basic group such as an amino group.

The hydrogen bond may, for example, be a bond originating from a hydroxyl group or an amido group.

The coordinate bond may, for example, be a bond between a metal and a ligand as observed in nitrilotriacetatic acid derivative-nickel-histidine.

The hydrophobic interaction may, for example, be an interaction between the hydrophobic area existing in particles having the inorganic material and the hydrophobic section of the organic dye.

The stacking interaction may, for example, be a pi-pi stacking of the aromatic ring existing in particles having the inorganic material and the aromatic ring of the organic dye.

Any known reaction can be utilized without limitations for the reaction for supporting the organic dye by particles having the inorganic material. An excessive amount of the organic dye may be used for each particle having the inorganic material in the supporting reaction.

If necessary, a solvent may be used for the supporting reaction. More specifically, particles having the inorganic material may be added to the solvent in which the organic dye is dissolved for conducting the supporting reaction.

Solvents that can be used for this embodiment include hydrocarbons such as hexane, cyclohexane and heptane, ketones such as acetone and methyl ethyl ketone, ethers such as dimethyl ether, diethyl ether and tetrahydrofuran, halogenated hydrocarbons such as dichloromethane, chloroform, carbon tetrachloride, dichloroethane and trichloroethane, aromatic hydrocarbons such as benzene and toluene, aprotic polar solvents such as N,N-dimethylformamide and dimethylsulfoxide, pyridine derivatives, buffer solutins such as phosphoric acid buffer, and water. Preferably, the solvent dissolves the organic dye. The rate at which the solvent is employed may be appropriately determined according to the rate of use of particles having the inorganic material, the rate of use of the organic dye and the reaction conditions of the supporting reaction.

While the reaction temperature of the supporting reaction is not subjected to any particular limitations, it is normally in the range between −30° C. and the boiling point of the solvent. Note, however, that an optimal temperature that matches the organic dye to be used, particles having the inorganic material and the reaction solvent may desirably be selected. While the reaction time cannot be determined in a simple manner, it is preferably in the range between 1 hour and 48 hours.

If necessary, the reaction solution of the supporting reaction can be removed by distillation. Alternatively, the reaction product can be isolated and purified from the reaction solution of the supporting reaction by means of size exclusion column chromatography, ultrafiltration or dialysis.

When conducting a reaction for causing particles having the inorganic material to support the organic dye, the number of organic dyes supported by each particle having the inorganic material can be increased by increasing the supplied quantity of the organic dyes per particle having the inorganic material, by raising the concentration of particles having the inorganic material or of the organic dyes in the reaction solution, by prolonging the reaction time and/or by raising the reaction temperature.

If it is assumed that particles having the inorganic material show a spherical profile, a particle can maximally support $1.5\times10^7$ of organic dyes in view of the surface area of the particle when the diameter of particles having the inorganic material is 1 μm.

When fluorescent dyes are employed as organic dyes, the efficiency of conversion of the energy of irradiated light to fluorescence falls and the efficiency of conversion to thermal energy rises as the number of organic dyes to be supported increases due to concentration quenching of the organic dyes. As the efficiency of conversion to thermal energy rises, the efficiency of conversion to an acoustic wave rises. The intensity of photoacoustic signal is high when the acoustic wave is large. Thus, as many organic dyes as possible are preferably supported to improve the intensity of photoacoustic signal. In other words, it is desirable to highly densely support organic dyes.

It is desirable to make particles highly densely support organic dyes in order to reduce the efficiency of conversion of the energy of irradiated light to fluorescence and raise the efficiency of conversion to an acoustic wave. As an example, a technique of preparing particles having the inorganic material that are coated with a branched polymer such as polyamide amine dendorimer having a large number of reactive functional groups on the surface or on which such a branched polymer is dispersed and making them support straight chain organic dyes such as cyanine-based dyes may be employed. Since straight chain organic dyes can react, while suppressing the steric repulsion of adjacent organic dyes, they can be made to be highly densely supported by particles having the inorganic material.

A contrast agent including particles having an inorganic material such as Resovist tends to accumulate in the liver. For this reason, when a site of pathological change other than the liver is to be imaged, it is necessary to improve the blood retention, suppressing the accumulation in the liver.

It is desirable to adjust the kinds and the number of organic dyes to be supported as means for improving the blood retention.

The contrast agent for photoacoustic imaging in which organic dyes are supported by particles having an inorganic material may have any mean particle size. When a site of pathological change is found in a blood vessel, the mean particle size is preferably between about 1 nm and about 1 μm. When, on the other hand, a site of pathological change is found outside blood vessels, an mean particle size between 1 nm and 500 nm, preferably between nm and 200 nm, is desirable from the viewpoint of transfer from the inside of a blood vessel to an tissue outside blood vessels and/or transfer from a tissue to another outside blood vessels.

(Techniques for Confirming Chemical Bonding of an Organic Dye to Particles Having the Inorganic Material)

Techniques for confirming chemical bonding of an organic dye to particles having the inorganic material that can be used for this embodiment include size exclusion column chromatography, ultrafiltration and dialysis.

When, for example, size exclusion column chromatography is employed, the organic dye that is chemically bonded to particles having the inorganic material is collected in a retention time different from the retention time that is required when the organic dye is isolated at the time of collection.

When ultrafiltration is employed, the organic dye that is chemically bonded to particles having the inorganic material is collected in a fraction different from the fraction that is involved when the organic dye is isolated at the time of collection.

Finally, when dialysis is employed, the organic dye that is supported by particles having the inorganic material is collected in the dialysis membrane whereas the organic dye that is isolated at the time of collection is collected outside the dialysis membrane.

(Specific Examples for Causing the Organic Dye to Be Supported by Particles Having the Inorganic Material)

Specific examples of particles having the inorganic material and supporting the organic dye that can be used for this embodiment include particles having the inorganic material coated with protein, particles having the inorganic material coated with a fatty acid, particles having gold as inorganic material, particles having semiconductor particles as inorganic material, particles having the inorganic material coated with a synthetic polymer and particles having the inorganic material coated with liposome.

As particles having the inorganic material coated with protein, for example, iron oxide particles carrying albumin on the surface (particle size 20 nm) (to be referred to as "iron oxide particles (1)" hereinafter) that are available from micromod Partikel-technologie can be employed.

As the organic dye, IRDye700DX NHS Ester (available from LI-COR) can be employed. The supporting reaction is conducted by adding a dimethyl sulfoxide solution of IRDye700DX NHS Ester into a phosphoric acid buffer at room temperature for 12 hours, while shielding light. After the reaction, the reaction product is purified by means of size exclusion column chromatography that is equilibrated with the phosphoric acid buffer. A contrast agent for photoacoustic imaging in which the organic dye is supported by particles having the inorganic material coated with protein can be obtained by subsequently concentrating the reaction product by ultrafiltration.

As particles having the inorganic material coated with a fatty acid, for example, iron oxide particles carrying an amino group on the surface (particle size 20 nm) (to be referred to as "iron oxide (2)" hereinafter) that are available from Ocean Nanotech can be employed.

As the organic dye, DyLight750DX NHS Ester can be employed. The supporting reaction is conducted by adding a dimethyl sulfoxide solution of DyLight750DX NHS Ester into a phosphoric acid buffer at room temperature for 6 hours, while shielding light. After the reaction, the reaction product is purified by means of size exclusion column chromatography that is equilibrated with the phosphoric acid buffer. A contrast agent for photoacoustic imaging in which the organic dye is supported by particles having the inorganic material coated with a fatty acid can be obtained by subsequently concentrating the reaction product by ultrafiltration.

As particles having gold particles as inorganic material, for example, gold nano particles carrying an amino group on the surface (particle size 1.4 nm) (to be referred to as "gold nano particles (1)" hereinafter) available from NANOPROBES can be employed.

As the organic dye, Cy5.5 Mono-reactive Dye (available from GE Healthcare Japan) can be employed. The supporting reaction is conducted by adding a dimethyl sulfoxide solution of Cy5.5 Mono-reactive Dye into a phosphoric acid buffer at room temperature for 3 hours, while shielding light. After the reaction, the reaction product is purified by means of size exclusion column chromatography that is equilibrated with the phosphoric acid buffer. A contrast agent for photoacoustic imaging in which the organic dye is supported by particles having gold as inorganic material can be obtained by subsequently concentrating the reaction product by ultrafiltration.

As particles having semiconductor particles as inorganic material, for example, semiconductor nano particles Qdot (tradename) 800 Streptavidin Conjugate carrying streptavidin on the surface (particle size 15 to 20 nm) (to be referred to as "semiconductor nano particles (1)" hereinafter) available from Invitrogen) can be employed.

As the organic dye, Cy5.5 Mono-reactive Dye can be employed. The supporting reaction is conducted by adding a dimethyl sulfoxide solution of Cy5.5 Mono-reactive Dye into a phosphoric acid buffer at room temperature for 3 hours, while shielding light. After the reaction, the reaction product is purified by means of size exclusion column chromatography that is equilibrated with the phosphoric acid buffer. A contrast agent for photoacoustic imaging in which the organic dye is supported by particles having semiconductor particles as inorganic material can be obtained by subsequently concentrating the reaction product by ultrafiltration.

As particles having the inorganic material coated with a synthetic polymer, iron oxide particles coated by means of polyethyleneimine as polymer can be employed. Such particles can be prepared by dispersing iron oxide particles into an aqueous solution of polyethyleneimine as coating technique. The amino group of the obtained iron oxide particles coated with polyethyleneimine can be made to react with a bi-functional linker, Succinimidyl 4-[N-maleimidomethyl] cyclohexane-1-carboxylate (available from PIERCE Biotechnology).

After the reaction, the particles can be made to support the organic dye by way of a reaction with Alexa Fluor 750 C5-maleimide that is a thiol-reactive dye. After the reaction, the product is purified by means of size exclusion column chromatography that is equilibrated with the phosphoric acid buffer. A contrast agent for photoacoustic imaging in which the organic dye is supported by particles having the inorganic material coated with a synthetic polymer can be obtained by subsequently concentrating the reaction product by ultrafiltration.

As particles having the inorganic material coated with liposome, particles prepared by using a lipid mixture of iron oxide particles, phosphatidylcholine, phosphatidylethanolamine and N-(6-maleimidocaproyloxy)-dipalmitoylphosphatidylethanolamine can be employed.

The amino group of the obtained iron oxide particles coated with liposome can be made to react with a bi-functional linker, Sulfosuccinimidyl 6-(3'-[2-pyridyldithio]-propionamido)hexanoate (available from PIERCE Biotechnology).

After the reaction, the particles can be made to support the organic dye by way of a reaction with Alexa Fluor 750 C5-maleimide that is a thiol-reactive dye (available from Invitrogen). After the reaction, the product is purified by means of size exclusion column chromatography that is equilibrated with the phosphoric acid buffer. A contrast agent for photoacoustic imaging in which the organic dye is supported by particles having the inorganic material coated with liposome can be obtained by subsequently concentrating the reaction product by ultrafiltration.

Embodiment 2

Now, a method of detecting a contrast agent for photoacoustic imaging will be described as Embodiment 2. The detection method of this embodiment includes the following steps of:

(1) administering the contrast agent for photoacoustic imaging of Embodiment 1 to a subject body;

(2) irradiating light in the wavelength region between 600 nm and 1,300 nm to the subject body; and (3) detecting the acoustic wave generated from the contrast agent existing in the subject body.

For the purpose of this embodiment, the expression of imaging refers to visualizing and imaging information on the substance that is the object of imaging by some measurement means. Examples of imaging include tomography for picking up an image of the object along a plane running through the object.

The contrast agent for photoacoustic imaging that is to be administered to the subject body is same as that of Embodiment 1, it will not be described here any further.

The device for generating light to be irradiated onto the subject body and the device for detecting the acoustic wave generated from the contrast agent for photoacoustic imaging existing in the subject body are not subjected to any particular limitations in the step (2).

EXAMPLES

Now, the present invention will be described further by way of examples in order to more clearly illustrate the features of the present invention. However, it should be noted that the present invention is by no means limited by the examples and the materials, the composing conditions, the reaction conditions described therein can be modified and altered so long as a contrast agent for photoacoustic imaging having similar functions and effects is obtained. The measurement of the acoustic wave can be paraphrased as measurement of a photoacoustic signal.

Example A-1

Synthesis of Photoacoustic Imaging Contrast Agent (A-1)

Iron oxide containing dextran particles having an amino group (particle size: 20 nm) (to be referred to as "iron oxide particles (3)" hereinafter) available from micromod Partikeltechnologie were employed as particles having an inorganic material.

A buffer exchange for a 0.05M carbonic acid buffer (pH=9.6) was realized by means of ultrafiltration. The iron content in the solution is quantitatively measured by a UV-VIS-NIR measurement (ultraviolet-visible-near infrared spectroscopy: Lambda Bio 40 available from Perkin Elmer). Seeing the results of the quantitative measurement of the iron content, the iron oxide particles (3) were made to show an iron concentration of 5.0 mg/ml by way of an adjustment process and employed for the following experiment.

Dimethyl sulfoxide was added to Alexa Fluor 750 succinimidyl ester reactive dye (available from Invitrogen, to be referred to as "Alexa750NHS" hereinafter) and the concentration was adjusted to 10 mg/ml. 10 ml of Alexa750NHS solution was added to an iron oxide particle (3) solution (400 uL) and the solution was gently stirred at room temperature for 4 hours. Subsequently, the solution was purified by means of size exclusion column chromatography that is equilibrated with the phosphoric acid buffer. Then, contrast agent for photoacoustic imaging (A-1) was obtained as a result of concentration by ultrafiltration.

FIG. 1 shows the results of a UV-VIS-NIR measurement of the prepared contrast agent for photoacoustic imaging (A-1). The number of supported organic dyes per iron oxide particle (3) and the molar absorption coefficient of the contrast agent (A-1) were determined by way of the UV-VIS-NIR measurement, following the conventional procedure. It was found that eleven Alexa750NHS were supported per iron oxide particle (3). The molar absorption coefficient of the contrast agent for photoacoustic imaging (A-1) at 710 nm was approximately about 2.0 times greater than that of the value obtained before supporting Alexa750NHS.

Comparative Example A-2

Alexa750 glycin that is not reactive to an amino group was prepared by causing Alexa750NHS and glycin with each other and employed in the following experiment.

Contrast agent for photoacoustic imaging (A-2) was prepared by mixing iron oxide particles (3) and Alexa750 glycin as an example of contrast agent that did not support any organic dye. The mixing ratio was adjusted so as to make it agree with the ratio of the iron oxide particles to the organic dye of the contrast agent (A-1).

Comparative Example A-3

A solution of iron oxide particles (3) of a quantity same as that of Example A-1 was prepared to obtain contrast agent for photoacoustic imaging (A-3).

Comparative Example A-4

A solution of Resovist containing iron, the quantity of which is same as that of Example A-1, was prepared to obtain contrast agent for photoacoustic imaging (A-4).

Example B-1

Synthesis of Contrast Agent for Photoacoustic Imaging B-1

106 mg of Poly(maleic anhydride-alt-1-octadecene) (available from Sigma-Aldrich Japan, to be referred to as "PMAO" hereinafter), 370 mg of mPEG-Amine having a weight average molecular weight of 5,000 (available from Laysan Bio, to be referred to "mPEG-NH2" hereinafter) and 76 mg of organic dye ADS832WS (available from American Dye Source) were dissolved in 20 ml of chloroform and the solution was stirred for 24 hours. After the reaction, the reaction product was purified by dialysis and the solvent was removed by distillation to obtain synthesized iron oxide particle coating agent supporting the organic dye (B-1).

The structure determination of the obtained compound was analyzed by $^{1}$H-NMR (FT-NMR: Bruker AVANCE 500; resonance frequency: 500 MHz; nuclide for measurement: $^{1}$H; temperature for the measurement: room temperature; solvent: deuterated chloroform).

13 mg of the iron oxide particle coating agent (B-1) and 4.4 mg of iron oxide particles SOR-50-50 (particle size: 50 nm) (available from Ocean Nanotech, to be referred to as "iron oxide particles (4)" hereinafter) were dissolved in 12.5 ml of tetrahydrofuran, which was stirred for 24 hours. Contrast agent for photoacoustic imaging (B-1) was obtained by purifying the product after the stirring.

The number of supported organic dyes per iron oxide particle (4) and the molar absorption coefficient of the contrast agent (B-1) were determined by way of a UV-VIS-NIR measurement, following the conventional procedure.

It was found that 460 ADS832WS were supported per iron oxide particle (4).

Comparative Example B-2

Contrast agent for photoacoustic imaging (B-2) was obtained by using iron oxide particles (4) and iron oxide particle coating agent (B-2) that did not support organic dye ADS832WS as an example where iron oxide particles did not support any organic dye.

The iron oxide particle coating agent (B-2) was synthesized as in Example (B-1) except that organic dye ADS832WS was not employed.

The molar absorption coefficient of the contrast agent (B-1) at 850 nm was about 2.0 times greater than that of the contrast agent (B-2) that did not support the organic dye.

Example C-1

Synthesis of Contrast Agent for Photoacoustic Imaging C-1

100 mg of PMAO and 370 mg of mPEG-NH2 were dissolved in 20 ml of chloroform and the solution was stirred for 24 hours. After the reaction, the reaction product was purified by dialysis and the solvent was removed by distillation to obtain synthesized iron oxide particle coating agent supporting the organic solvent (C-1).

6.3 mg of iron oxide particle coating agent (C-1), 2.2 mg of iron oxide particles (4) and 2,11,20,29-Tetra-tert-butyl-2,3-naphthalocyanine (available from Sigma-Aldrich Japan, to be referred to as "t-Bu Nc" hereinafter) were dissolved in 5.7 ml of chloroform, which was then stirred for 18 hours. After the stirring, purification was performed by dialysis. Contrast agent for photoacoustic imaging (C-1) was obtained by washing out the organic dye that was not supported by iron oxide particles by means of a magnetic column and collecting only the iron oxide particle supporting the organic dye.

Figure 3:
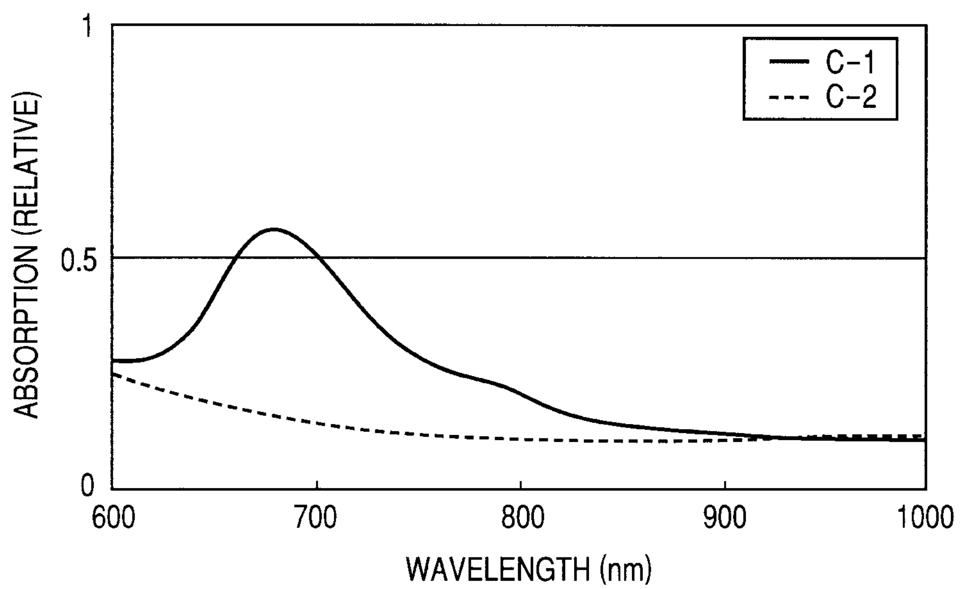
FIG. 3 is an illustration of the results of measurement of the light absorbance of the contrast agent for photoacoustic imaging of Example C-1 and that of the contrast agent of Comparative Example C-2.

FIG. 3 shows the results of a UV-VIS-NIR measurement of the prepared contrast agent for photoacoustic imaging (C-1). The number of supported organic dyes per iron oxide particle (4) and the molar absorption coefficient of the contrast agent (C-1) were determined by way of the UV-VIS-NIR measurement, following the conventional procedure. It was found that 43,000 t-Bu Nc were supported per iron oxide particle (4).

Comparative Example C-2

Contrast agent for photoacoustic imaging (C-2) was obtained by using iron oxide particles (4) and iron oxide particle coating agent (B-2) as in Comparative Example (B-2) as an example where iron oxide particles did not support any organic dye.

The molar absorption coefficient of the contrast agent (C-1) at 710 nm was about 2.6 times greater than that of the contrast agent (C-2) that did not support the organic dye.

Example D-1

Synthesis of Contrast Agent for Photoacoustic Imaging (D-1)

Iron oxide containing dextran particles having an amino group (particle size: 50 nm) (to be referred to as "iron oxide particles (5)" hereinafter) available from micromod Partikeltechnologie were employed as particles having an inorganic material.

The reaction was conducted by means of a carbonic acid buffer (pH=8).

HiLyte Fluor™ 750 Bis-NHS ester, isomer II TEA salt (available from ANASPEC, to be referred to as "HiLyte Fluor 750" hereinafter) was added to make the ratio the supplied number of dyes/particles (the mol ratio of the supplied dye relative to the iron oxide particles (5)) equal to 86.

The mixture was gently stirred at room temperature for 1 hour and contrast agent for photoacoustic imaging (D-1) was obtained by purifying the reaction product by ultrafiltration.

The number of supported organic dyes per iron oxide particle (5) and the molar absorption coefficient of the contrast agent (D-1) were determined by way of the UV-VIS-NIR measurement, following the conventional procedure. It was found that 23 HiLyte Fluor 750 were supported per iron oxide particle (5).

The molar absorption coefficient of the contrast agent for photoacoustic imaging (D-1) at 750 nm was approximately 1.3 times greater compared to the value obtained before supporting HiLyte Fluor 750.

(Example D-2) Through (Example D-5)

Synthesis of Contrast Agents for Photoacoustic Imaging (D-2) Through (D-5)

Contrast agents for photoacoustic imaging (D-2) through (D-5) were obtained as in Example (D-1) except that ratios of the supplied number of dyes/particles were respectively be made equal to 535, 1,069, 5,347 and 10,694.

Table A below summarily shows the supplied number of dyes/particles, the supported number of dyes/particles and the molar absorption coefficients of the particles.

It was found that the supported number of dyes/particles increases if the supplied number of dyes/particles increases.

The molar absorption coefficient of the contrast agent for photoacoustic imaging (D-5) at 750 nm supporting 395 dyes was approximately 9.2 times greater if compared with the value obtained before supporting HiLyte Fluor 750.

TABLE A

Supplied number of dyes/particles, supported number of dyes/particles and molar absorption coefficient of particles

| | Supplied number of dyes | Supported number of dyes | Molar absorption coefficient of particles |
|---|---|---|---|
| | 0 | 0 | $1.3 \times 10^7$ |
| D-1 | 86 | 23 | $1.7 \times 10^7$ |
| D-2 | 535 | 63 | $2.7 \times 10^7$ |
| D-3 | 1069 | 108 | $4.1 \times 10^7$ |
| D-4 | 5347 | 332 | $1.0 \times 10^8$ |
| D-5 | 10694 | 395 | $1.2 \times 10^8$ |

molar absorption coefficient of iron oxide particles (5) at 750 nm before the support = $1.3 \times 10^7\ M^{-1} \cdot cm^{-1}$
molar absorption coefficient of HiLyte Fluor 750 at 750 nm = $2.5 \times 10^5\ M^{-1} \cdot cm^{-1}$

Example E-1

Synthesis of Contrast Agent for Photoacoustic Imaging (E-1)

SOR-10-50 (particle size: 10 nm) (available from Ocean Nanotech, to be referred to as "iron oxide particles (6)" hereinafter) was employed as iron oxide particles.

Indocyanine Green (a standard item not listed in the Japanese Official Pharmacopocial Reference, to be referred to as "ICG" hereinafter) was employed as organic dye to be supported.

The material for preparing particles having the inorganic material supporting an organic dye of this example was prepared by means of the method described below, using a phospholipid, a polyoxyethylene sorbitan-based fatty acid ester and a polymer.

Iron oxide particles (6) (13.8 mg) and a copolymer of polylactic acid and glycolic acid (9.2 mg) were added to chloroform (1 ml) and an ultrasonic wave was irradiated onto the mixture in an ultrasonic bath for 10 minutes to prepare a chloroform solution.

5.2 mg of ICG and 8.3 mg of nicotinic acid amide were added to the chloroform solution to prepare a mixture chloroform solution of the inorganic material and the organic dye.

Subsequently, the chloroform solution was added to an aqueous solution (12 ml) where Tween20 (60 mg) and a phospholipid (7.3 mg, DSPE-PEG-MAL, N-[(3-Maleimide-1-oxopropyl)aminopropyl polyethyleneglycol-carbamyl] distearoylphosphatidyl-ethanolamine, available from NOF Corporation) were dissolved to produce a mixture solution.

An O/W type emulsion was prepared by subsequently processing the mixture solution by means of an ultrasonic disperser for 4 minutes.

Thereafter, the chloroform was removed by distillation from the dispersoid, reducing the pressure to the emulsion 100 hPa for more than 1 hour at 40° C. The solvent was removed by distillation and the product was purified by dialysis. After the dialysis, particles were collected by centrifugation to obtain contrast agent for photoacoustic imaging (E-1).

Figure 4:
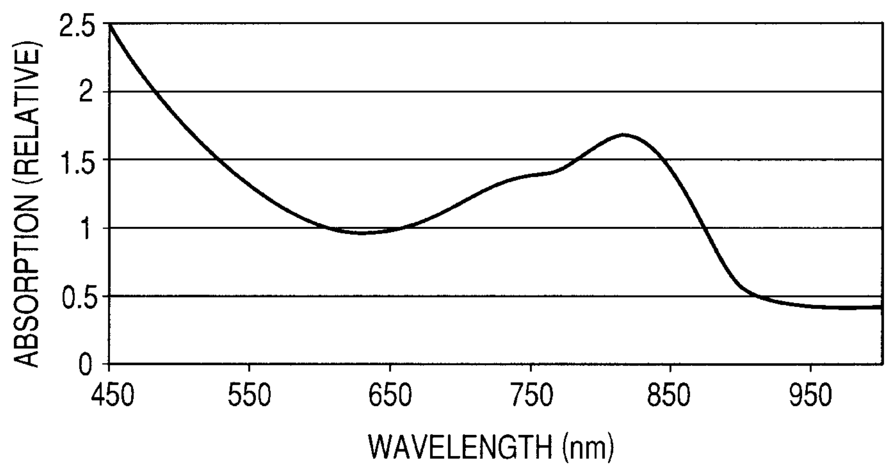
FIG. 4 is an illustration of the results of measurement of the light absorbance of the contrast agent for photoacoustic imaging of Example E-1.

FIG. 4 shows the results of a UV-VIS-NIR measurement of the prepared contrast agent for photoacoustic imaging (E-1). The number of supported organic dyes per iron oxide particle (6) and the molar absorption coefficient of the contrast agent (E-1) were determined by way of the UV-VIS-NIR measurement, following the conventional procedure.

It was found that each particle contained 103 iron oxide particles (6) and 6,978 ICG were supported.

Example 1 of Evaluation of Photoacoustic Characteristics

Photoacoustic signals were measured by referring to Japanese Patent Application Laid-Open No. H06-296612. The measurement conditions are shown below.

Type Titanium Sapphire Laser (available from Lotis) was employed as light source and the measurement conditions included: wavelength: 710 nm, energy density: 12 mJ/cm$^2$, pulse width: 20 nanosec, pulse repetition: 10 Hz.

Ultrasonic transducer Type V303 (available from Panametrics-NDT) was employed for the measurement with measurement conditions including central band: 1 MHz, element size: 13 mm, measurement distance: 25 mm (non-focus), amp: +30 dB (ultrasonic amp Model 5682, available from Olympus).

A cuvet with a light path length of 0.1 cm (made of polystyrene) was employed as measuring container. DPO4104 (available from Techtoronics) was employed as measuring instrument and data was collected using a detection of photoacoustic light by means of a photodiode as trigger, using the averages of 128 measured values (128 pulses).

The contrast agents (A-1) through (A-4) were evaluated for the photoacoustic signal characteristics observed at wavelength of 710 nm.

Figure 2:
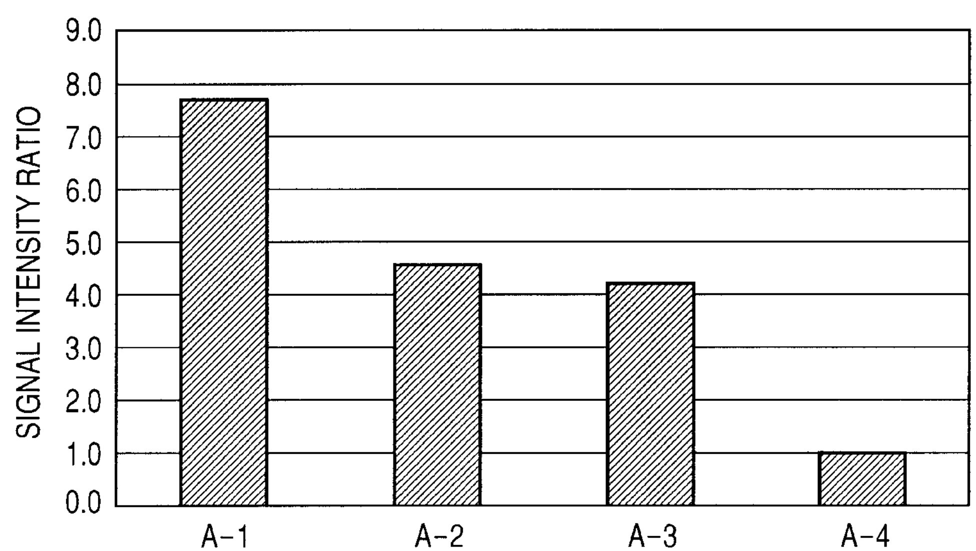
FIG. 2 is an illustration of the results of evaluation of the photoacoustic characteristic of the contrast agent for photoacoustic imaging of Example A-1 and those of the contrast agents of Comparative Examples A-2 through A-4.

FIG. 2 summarily shows the results obtained by determining the signal intensities of the contrast agents (A-1) through (A-4) as ratios relative to the contrast agent (A-4), when the signal intensity per unit particle of the contrast agent (A-4) was defined to be 1.

The contrast agent (A-1) where particles having iron oxide supported an organic dye by way of chemical bonding showed a high signal intensity relative to the contrast agent (A-3) of particles having only iron oxide and the Resovist (A-4).

The contrast agent (A-1) where particles having iron oxide supported an organic dye by way of chemical bonding showed a high signal intensity compared to the contrast agent (A-2) where no organic dye was supported by way of chemical bonding.

Table 1 summarily shows the degrees of absorption of light at 710 nm (relative values) observed in the measurements of degrees of absorption of light before and after the evaluation of the photoacoustic signal characteristics. The contrast agent (A-2) where no organic dye was supported by way of chemical bonding showed a remarkable fall in the degree of absorption of light after the evaluation of the photoacoustic signal characteristics, which suggests that organic dyes are decomposited. On the other hand, the contrast agent (A-1) where an organic dye was supported by way of chemical bond substantially did not show any change in the degree of absorption of light.

TABLE 1

| | before evaluation | after evaluation |
|---|---|---|
| A-1 | 1.6 | 1.5 |
| A-2 | 1.7 | 1.1 |
| A-3 | 1 | 1.1 |
| A-4 | 0.7 | 0.8 |

* relative value when the degree of absorption of light of the contrast agent (A-3) before the evaluation of the photoacoustic signal characteristics was defined to be 1.

Example 2 of Evaluation of Photoacoustic Characteristics

Photoacoustic signals were measured by referring to Japanese Patent Application Laid-Open No. H06-296612. The measurement conditions are shown below.

Liquid measurement cell: A liquid measurement cell similar to the one in Example 1 of evaluation was employed.

Light source: A light source similar to the one in Example 1 of evaluation was employed.

Pulse light energy: 18 mJ (wavelength 710 nm), 18 mJ (wavelength 850 nm).

Primary excitation laser: Nd/YAG laser LS-2134 (available from Lotis TII).

Primary excitation wavelength: 532 nm (secondary higher harmonic).

Primary excitation pulse width: 16 through 18 ns.

Primary excitation pulse energy: 150 mJ, repetition frequency: 10 Hz.

Water immersion type ultrasonic probe: A probe similar to the one in Example 1 of evaluation was employed.

Preamp: Model 5682 (available from Olympus), degree of amplification: +30 dB, cutoff frequency: 30 MHz.

Oscilloscope: An oscilloscope similar to the one in Example of evaluation was employed.

Laser beam detecting photodiode: DET10A/M (available from THORLABS)

Measurement method: A liquid measurement cell was filled with the sample dispersion solution and its laser beam irradiation site was immersed in a glass container filled with water for photoacoustic measurement. The emission wavelength of a titanium sapphire laser was set to a predetermined wavelength and a laser pulse beam was irradiated to the laser beam irradiation site from a surface of the cell. The water immersion type ultrasonic probe was placed at a position separated from the surface by 25 mm and opposite to the surface for the irradiation of laser beam and the electric signal generated as a photoacoustic signal was input to the probe was amplified by the preamp. The amplified signal was then input to the oscilloscope. Additionally, dispersed light that was generated as the laser pulse beam hit the measurement cell was turned into an electric signal by means of a photodiode and input to the oscilloscope as trigger signal. The input voltage waveform obtained by accumulating and averaging 128 signals by means of the averaging/processing function that the oscilloscope had was used as evaluation waveform of the photoacoustic signal of the sample dispersion solution. The difference between the positive peak voltage and the negative peak voltage was used as evaluation value of the photoacoustic signal intensity.

The contrast agents (B-1) and (B-2) were evaluated for photoacoustic signal characteristics at wavelength 850 nm.

The signal intensity of the contrast agent (B-2) was defined to be 1. The ratio of the signal intensity of the contrast agent (B-1) relative to the signal intensity of the contrast agent (B-2) was 1.2 to prove a high signal intensity for the contrast agent (B-1). Additionally, the signal intensity of the contrast agent (B-1) was 279 times as high as the signal intensity per unit particle of the Resovist.

The degree of absorption of light of the contrast agent (B-1) was observed before and after the evaluation of the photoacoustic signal characteristics. No fall in the degree of absorption of light was observed.

The contrast agents (C-1) and (C-2) were evaluated for photoacoustic characteristics at wavelength 710 nm.

The signal intensity of the contrast agent (C-2) was defined to be 1. The ratio of the signal intensity of the contrast agent (C-1) relative to the signal intensity of the contrast agent (C-2) was 3.2 to prove a high signal intensity for the contrast agent (C-1). Additionally, the signal intensity of the contrast agent (C-1) was 1,118 times as high as the signal intensity per unit particle of the Resovist.

The degree of absorption of light of the contrast agent (C-1) was observed before and after the evaluation of the photoacoustic signal characteristics. No fall in the degree of absorption of light was observed.

Example 3 of Evaluation of Photoacoustic Characteristics

The contrast agents (D-1) through (D-5) were evaluated for photoacoustic signal characteristics at wavelength 750 nm by means of a method similar to that of Example 2.

For the purpose of comparison, iron oxide particles (5) and HiLite Fluor 750 (to be referred to as "unfixed dye" hereinafter) not supported by iron oxide particles (5) were also evaluated for photoacoustic signal characteristics.

The fluorescence intensities of the contrast agents (D-1) through (D-5) and the free dye were measured by means of a fluorescence measuring instrument (fluorophotometer: F-4500 type spectrofluorophotometer, available from Hitachi) (excitation wavelength; 757 nm, fluorescence intensity at fluorescence wavelength of 780 nm).

Figure 5:
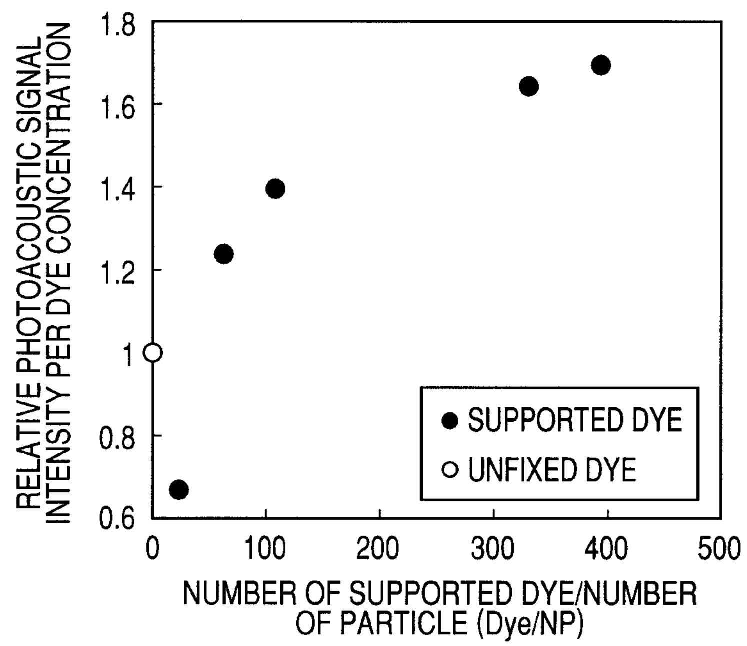
FIG. 5 is a summarized illustration of the relationship of the photoacoustic signal intensity standardized by dye concentration and the number of supported dyes per unit particle (to be expressed by "number of supported dyes/particle" hereinafter) obtained as a result of evaluation of the photoacoustic characteristics of the contrast agents for photoacoustic imaging in Examples D-1 through D-5.
Figure 6:
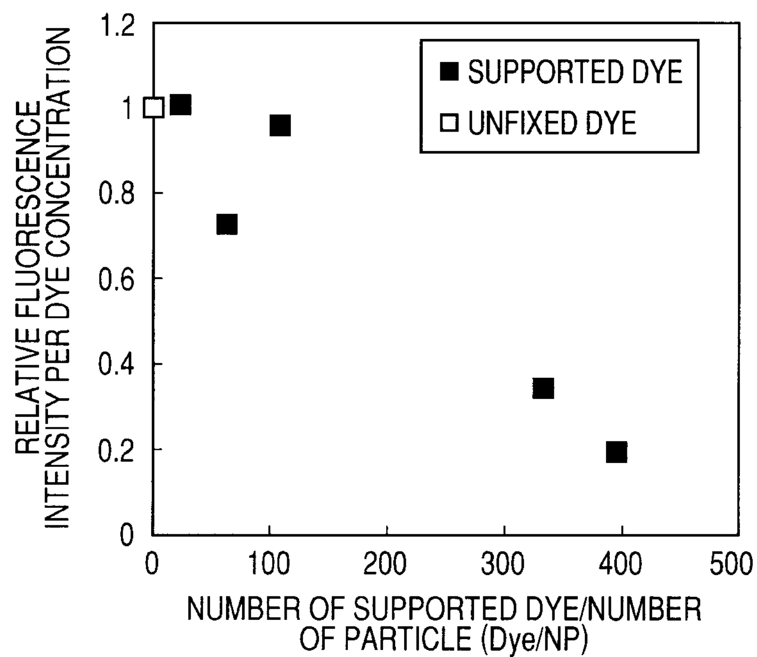
FIG. 6 is a summarized illustration of the relationship of the fluorescence intensity standardized by dye concentration and the number of supported dyes/particle obtained as a result of evaluation of the photoacoustic characteristics of the contrast agents for photoacoustic imaging in Examples D-1 through D-5.

FIGS. 5 and 6 summarily show the obtained results. FIG. 5 is a summarized illustration of the relationship of the photoacoustic signal intensity standardized by dye concentration and the number of supported dyes/particle. The photoacoustic signal intensities from the dyes of the contrast agents (D-1) through (D-5) varied within a range between 0.6 and 1.7 times of the photoacoustic signal intensity of the free dye. The photoacoustic intensity per dye was high when the number of supported dyes/particle was large.

The photoacoustic signal intensity from the contrast agent (D-5) that showed the largest number of supported dyes per particle was twice as high as the photoacoustic signal intensity of the free dye.

FIG. 6 summarized illustration of the relationship of the fluorescence intensity standardized by dye concentration and the number of supported dyes/particle. The fluorescence intensities from the dyes of the contrast agents (D-1) through (D-5) decreased as the number of supported dyes per particle increased. The fluorescence intensity of the contrast agent (D-5) having the largest number of supported dyes per particle showed a decrease of about 20% relative to the fluorescence intensity of the free dye. It may be easy to assume that this is attributable to a phenomenon that the inter-dye distance decreases to give rise to concentration quenching as the number of supported dyes per particle increases.

From the above results, it has become clear that an increase in the number of supported dyes per particle reduces the fluorescence quantum yield of dye to enable to produce an increase of nonradiative transitions and that of photoacoustic signal intensity.

Example 4 of Evaluation of Photoacoustic Characteristics

The contrast agent (E-1) was evaluated for photoacoustic signal characteristics at wavelength 800 nm by means of a method similar to that of Example 2.

The ratio of the signal intensity of the contrast agent (E-1) was 3,833 times as high as the signal intensity per unit particle of the Resovist.

The degree of absorption of light of the contrast agent (E-1) was observed before and after the evaluation of the photoacoustic signal characteristics. No fall in the degree of absorption of light was observed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2009-231999, filed Oct. 5, 2009, 2010-124075 filed May 31, 2010 which are hereby incorporated by reference herein in their entirety.

What is claimed is:

1. A contrast agent for photoacoustic imaging comprising:

a particle containing at least one inorganic material, said particle having at least six organic dyes covalently bonded thereto.

2. The contrast agent according to claim 1, wherein the inorganic material is at least one of metal oxide, noble metal colloid, semiconductor particles, an inorganic dye or an inorganic pigment.

3. The contrast agent according to claim 1, wherein the mean particle size of the contrast agent is in the range between 1 nm and 1,000 nm.

4. The contrast agent according to claim 1, wherein at least one of the organic dyes is a compound selected from the group consisting of

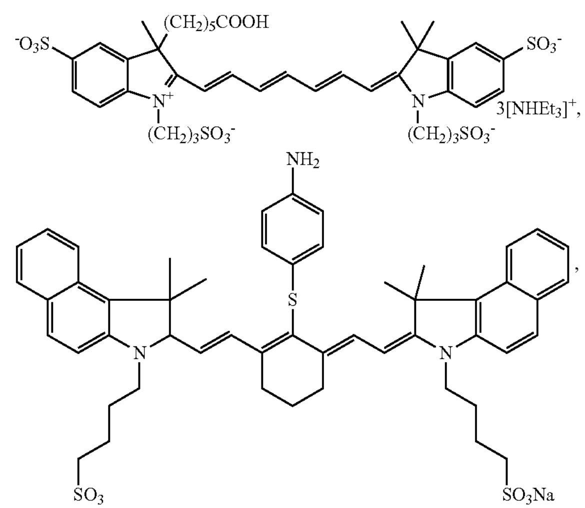

-continued

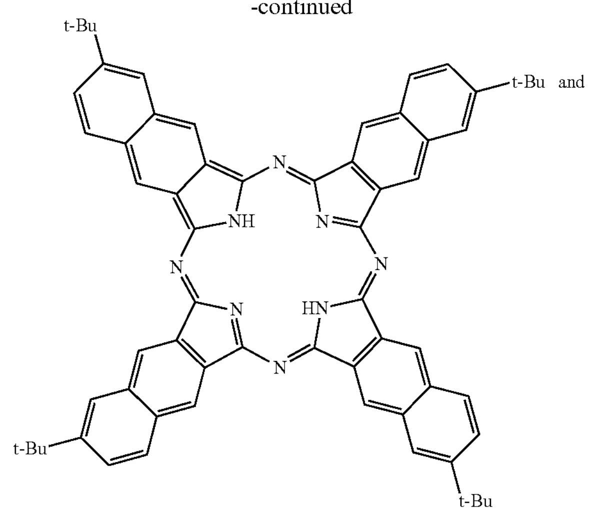

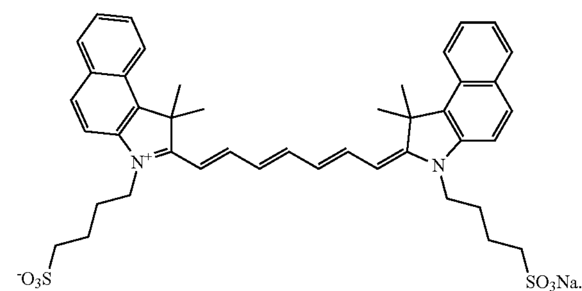

5. A photoacoustic imaging method comprising the steps of:

administering the contrast agent of claim 1 to a subject, irradiating light having a wavelength of between 600 nm and 1,300 nm onto the subject; and detecting the acoustic wave generated from the contrast agent administered to the subject.

6. A photoacoustic imaging method comprising:

administering the contrast agent of claim 1 to a subject wherein at least one organic dye has a molar absorption coefficient not less than 10 $M^{-1}cm^{-1}$ in the wavelength region between 600 nm and 1,300 nm and said inorganic material has a molar absorption coefficient not less than $10^2$ $M^{-1}cm^{-1}$ in the wavelength region between 600 nm and 1,300 nm;

irradiating light having a wavelength of between 600 nm and 1,300 nm onto the subject; and detecting the acoustic wave generated from the contrast agent administered to the subject.

7. The method according to claim 6, wherein the inorganic material is at least one of metal oxide, noble metal colloid, semiconductor particles, an inorganic dye or an inorganic pigment.

8. The method according to claim 6, wherein the inorganic material is iron oxide particles.

9. The method according to claim 6, wherein at least one of the six organic dyes is a compound selected from the group consisting of

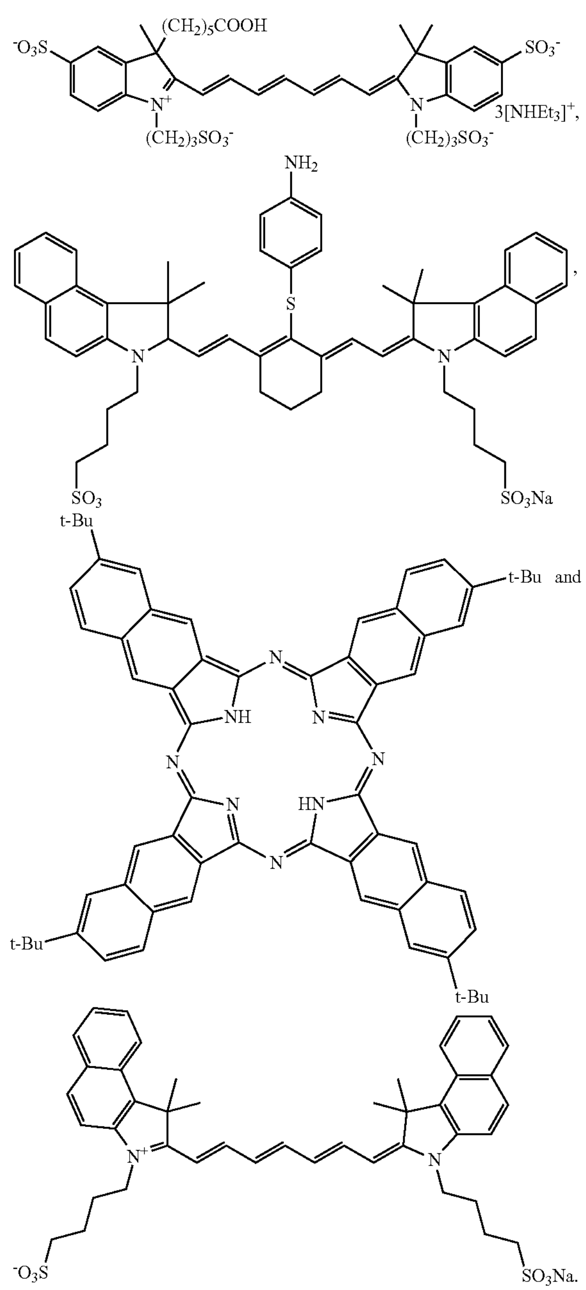

10. The contrast agent according to claim 1, wherein the inorganic material is metal oxide.

11. The contrast agent according to claim 1, wherein the particle further comprises a polysaccharide coating the inorganic material.

12. The contrast agent according to claim 11, wherein the organic dyes are covalently bonded to the polysaccharide.

13. The contrast agent according to claim 11, wherein the inorganic material is at least one of metal oxide, noble metal colloid, semiconductor particles, an inorganic dye or an inorganic pigment.

14. The contrast agent according to claim 11, wherein the inorganic material is metal oxide.

15. The contrast agent according to claim 11, wherein at least one of the organic dyes is a compound selected from the group consisting of

16. The contrast agent according to claim 11, wherein the polysaccharide is dextran.

17. The contrast agent according to claim 16, wherein the dextran comprises one or more amino, hydroxyl, carboxyl or maleimide groups.

* * * * *